United States Patent [19]

Qi

[11] Patent Number: 5,336,806
[45] Date of Patent: Aug. 9, 1994

[54] PURIFICATION OF 2,4,5-TRIFLUOROBENZOIC ACID

[75] Inventor: Jian S. Qi, Amherst, N.Y.

[73] Assignee: Occidental Chemical Corporation, Niagara Falls, N.Y.

[21] Appl. No.: 122,947

[22] Filed: Sep. 20, 1993

[51] Int. Cl.$^5$ .................. C07C 51/46; C07C 51/43; C07C 51/42
[52] U.S. Cl. .................... 562/494; 562/479; 562/493
[58] Field of Search .................... 562/479, 494

[56] References Cited

PUBLICATIONS

Gattermann, "The Practical Methods of Organic Chemistry," Macmillan Co. (1896), pp. 42–43.
CA 118(14):133182n (1992).
CA 101(14): 122338r (1984).
N. J. O'Reilly et al., Synlett Letters, Oct. 1990, "An Expedient Route to the Quinolone Antibacterial Intermediate, 2,4,5-Trifluorobenzoic Acid".
CA 114(11): 101357z (1990).
CA 110(1): 7855f (1987).
CA 108(22): 188895w (1986) and CA83(9): 79076z (1974).

Primary Examiner—Jose' G. Dees
Assistant Examiner—Barbara S. Frazier
Attorney, Agent, or Firm—Wayne A. Jones; Richard D. Fuerle

[57] ABSTRACT

Disclosed is a process for isolating and purifying 2,4,5-trifluorobenzoic acid from a solution in a decarboxylating solvent such as NMP. The solution is neutralized with a hydroxide. This results in the formation of a salt of the 2,4,5-trifluorobenzoic acid, which precipitates. The slurry is filtered to collect the precipitated salt and the precipitated salt is dissolved in water. The aqueous solution of the salt is then acidified which results in the reformation and precipitation of the 2,4,5-trifluorobenzoic acid.

3 Claims, No Drawings

PURIFICATION OF 2,4,5-TRIFLUOROBENZOIC ACID

BACKGROUND OF THE INVENTION

This invention relates to a process for purifying and isolating 2,4,5-trifluorobenzoic acid from a solvent such as N-methylpyrrolidone. In particular, it relates to a method in which soluble 2,4,5-trifluorobenzoic acid is converted into an insoluble salt then back into the acid again.

2,4,5-Trifluorobenzoic acid (2,4,5--TiFBA) is used as an intermediate in preparing quinolone antibacterials. It is prepared by a process that begins with tetrachlorophthalic anhydride. Tetrachlorophthalic anhydride is first hydrodechlorinated in NaOH/Zn to produce 3,4,6-trichlorophthalic acid, followed by imidization using methylamine to form 3,4,6-trichloro-N-methylphthalimide. That product is fluorinated by KF to form 3,4,6-trifluoro-N-methyl phthalimide, which is hydrolyzed to produce 3,4,6-trifluorophthalic acid. Decarboxylation results in a solution of 2,4,5-TiFBA in an organic decarboxylating solvent such as N-methylpyrrolidone (NMP).

The solution also contains an isomer of the acid, 2,3,5-trifluorobenzoic acid (2,3,5-TiFBA), as well as other contaminants. The removal of the 2,3,5-TiFBA can be accomplished by recrystallization, but the yield is low. Morever, it is very difficult to separate the 2,4,5-TiFBA from NMP by distillation because they appear to form an azeotrope. NMP also has a very strong affinity for TiFBA and clean-up of even a trace amount of NMP contamination requires high vacuum (<1 mm Hg) drying or chromatography. Moreover, if the solution is heated for too long it darkens and the TiFBA product decomposes, which is unacceptable for a highly pure substance to be used in making drugs. Even if the NMP is removed, the product very often must still undergo recrystallizations to remove the 2,3,5- isomer and other contaminants. All these involve lengthy steps and are not suitable for industrial applications. An article by Neil J. O'Reilly et al. in Synlett Letters, October 1990, pp. 609–610, titled "An Expedient Route To The Quinolone Antibacterial Intermediate, 2,4,5-Trifluorobenzoic Acid," describes a purification method which involves vacuum desiccation and chromatography, but that method requires stringent process conditions and equipment and is not suitable for mass production in industry.

SUMMARY OF THE INVENTION

I have discovered a method of purifying 2,4,5-TiFBA which separates it from NMP, 2,3,5-TiFBA and other impurities and is suitable for commercial scale application. In the process of this invention, I am able to separate 2,4,5-TiFBA from NMP by converting the 2,4,5-TiFBA into a salt. I have discovered that while 2,4,5-TiFBA is soluble in NMP, its salt is not soluble in NMP and it precipitates. This allows a simple separation of NMP by filtration.

Surprisingly, I have found that 2,3,5-TiFBA can also be completely removed during the removal of NMP, perhaps due to the higher solubility of its salt in the NMP/water mixture. After NMP is separated from the 2,4,5-TiFBA salt, converting the salt back to a precipitated acid product form in water further purifies the product, probably because the 2,3,5 acid is more soluble in water than is 2,4,5-TiFBA.

While recrystallization usually relies on a solubility difference in a solvent at different temperatures and has not been found to produce a high yield for purifying 2,4,5-TiFBA, the process of this invention actually has an unexpectedly high yield of 92%.

Therefore, by simply converting the product acid into salt and then back to acid, I am able to achieve both objectives of removing/recovering NMP solvent and purifying 2,4,5-TiFBA in the same sequence and with a high yield. Furthermore, the process consists of simple unit operation procedures and requires only mild process operating conditions. The equipment requirement is also simple. These valuable features make the process relatively easy and feasible for adaptation into commercial scale.

DESCRIPTION OF THE INVENTION

The starting material for the process of this invention is a solution of 2,4,5-TiFBA in an organic solvent. The solution contains various contaminants from previous reaction steps (hydrodechlorination, fluorination, hydrolysis and decarboxylation), in particular, usually about 5 to about 12 wt %, based on solids, of 2,3,5-TiFBA. The solution is typically about 10 to about 50 wt % solids and the solvent is typically an organic decarboxylating solvent such as dimethylsulfoxide, NMP, dimethylacetamide, dimethylsulfone, sulfolane, or dimethylformamide. Preferably, the solvent is NMP because producing 2,4,5-TiFBA in NMP results in a higher ratio of the 2,4,5- isomer to the 2,3,5- isomer and a shorter reaction time. A description of a typical preparation of the starting material can be found in the hereinabove-cited article by Neil J. O'Reilly et al., herein incorporated by reference.

In the first step of the process of this invention, the impure solution of 2,4,5-TiFBA in the organic decarboxylating solvent is mixed with an aqueous solution of an alkali metal or alkaline earth metal hydroxide. The amount of hydroxide used should be about stoichiometric with the amount of acid present, although up to about 10 wt % in excess of stoichiometric can be used to ensure a complete reaction. To limit the amount of water that must be removed in later steps, the solution should be as concentrated as possible. Examples of suitable hydroxides include sodium hydroxide, potassium hydroxide, calcium hydroxide, and magnesium hydroxide. Alkali metal hydroxides are preferred, and sodium hydroxide is particularly preferred as the reaction with sodium hydroxide is relatively simple. The addition of the hydroxide results in the formation and precipitation of the 2,4,5-TiFBA salt. The 2,3,5-TiFBA salt, which also forms, remains in the NMP/water mixture.

The second step of the process of this invention is optional, but it is preferably performed in order to increase the yield of the product. This step involves the removal of water and it is believed to be beneficial because it may further reduce the solubility of the 2,4,5-TiFBA in any NMP-water mixture that remains. The water is most easily removed by adding a substance with which water forms an azeotrope and heating the slurry to evaporate the azeotrope. Examples of azeotropic solvents include toluene, octane, butylacetate, ethylacetate, and methyl isobutyl ketone. Toluene is preferred because its azeotrope has a low boiling point and it works well.

In the third step of the process of this invention, the slurry formed in the first step is filtered to separate the 2,4,5-TiFBA salt from the organic solvent.

In an optional step, which is preferably performed, the collected 2,4,5-TiFBA salt is washed with a liquid that is a non-solvent for the salt but is a solvent for the decarboxylating solvent. This step will increase the yield of the product because, when the salt is converted back into the acid, some of the acid will dissolve in any remaining NMP-water mixture. Examples of suitable washing liquids include toluene, butyl acetate, ethyl acetate, octane, and methyl isobutyl ketone. Toluene is again preferred if it has been used as an azeotrope with water.

In the next step of the process of this invention, the 2,4,5-TiFBA salt is dissolved in water to form a solution of about 5 to about 50 wt % solids. The solution is preferably about 10 to about 20 wt % solids because if the solution is too concentrated water insoluble isomers or other contaminants may become trapped in the product.

In the next step, which is optional but is preferably performed, the aqueous solution is passed through a decolorizing agent to remove colored contaminants. Examples of suitable decolorizing agents include activated carbon, clay, zeolites, and activated alumina. The preferred decolorizing agent is activated carbon because it is very effective.

In the next step of this invention, the salt is acidified to produce 2,4,5-TiFBA, which precipitates. Any acid stronger than 2,4,5-TiFBA can be used, but it is preferable to use a strong mineral acid such as hydrochloric acid, sulfuric acid, nitric acid, phosphoric acid, hydrofluoric acid, or sulfonic acid. Sulfuric acid is preferred as it is inexpensive, can be very concentrated, and works well. The amount of acid used should be about stoichiometric with the amount of 2,4,5-TiFBA salt, although an excess of up to 100 wt % may be desirable.

In the final step, the precipitated 2,4,5-TiFBA is collected, such as by filtration. If desired, it can then be washed, for example, with water, and dried. The product is useful in making quinolone antibacterials. In the first footnote of the hereinabove-cited article by Neil J. O'Reilly a number of references are cited which describe the use of 2,4,5-TiFBA in the preparation of quinolone antibacterial agents.

The following examples further illustrate this invention.

EXAMPLE 1

For decarboxylation, 10 g of 3,4,6-trifluorophthalic acid (purity: 94% gas chromatography (GC) area) was dissolved in about 50 mL NMP. After decarboxylation at 190° C. for about 3.5 hours, a GC analysis showed approximately 88% 2,4,5-TiFBA (91% yield), 8% 2,3,5-TiFBA and 4% various by-products from pre-decarboxylation reaction steps. When the mixture was cooled and neutralized with 2.1 g NaOH dissolved in 8 mL water, precipitation of the 2,4,5 salt occurred. A GC analysis of the neutralized liquor (pH 6 to 6.5) also indicated that almost all of the 2,4,5-TiFBA had been converted into its sodium salt. Water in the mixture was removed along with most of the NMP by vaporization at 100 to 110° C. and 7 to 20 mm Hg to obtain the 2,4,5-TiFBA--Na salt. The salt, after being washed with ethyl acetate (5×50 mL), was dissolved in water and decolorized at 100° C. with 2 g of activated carbon. After the carbon had been filtered off, acidification by 5 ml 69% sulfuric acid gave a white 2,4,5-TiFBA precipitate, which was recovered by filtration. The final dried product was white, weighed 6.3 g and had a 2,4,5-TiFBA purity of greater than 99.7 wt %. Thus, the overall yield for both the decarboxylation and the product isolation/purification was 84%, while the isolation/purification had about a 92% yield.

EXAMPLE 2

This example is similar to Example 1 except that water in the 2,4,5-TiFBA--Na salt/NMP mixture was removed by azeotropic distillation using toluene to give a complete precipitation of 2,4,5-TiFBA-Na salt. The salt was then recovered by filtration and washed with toluene. The yield was similar to Example 1 and the purity of 2,4,5-TiFBA obtained was 99.4%.

I claim:

1. A method of isolating and purifying 2,4,5-trifluorobenzoic acid from a first solution of about 10 to about 50 wt % solids in N-methyl pyrrolidone which contains about 5 to about 8 wt % 2,3,5-trifluorobenzoic acid comprising:
   (A) adding to said first solution about a stoichiometric amount of sodium hydroxide, whereby the sodium salt of 2,4,5-trifluorobenzoic acid precipitates forming a slurry;
   (B) adding toluene to said slurry and evaporating toluene-water azeotrope from said slurry;
   (C) filtering said slurry to collect said sodium salt of 2,4,5-trifluorobenzoic acid;
   (D) washing said sodium salt of 2,4,5-trifluorobenzoic acid with toluene;
   (E) dissolving said sodium salt of 2,4,5-trifluorobenzoic acid in water to form a second solution of about 5 to about 50 wt % solids;
   (F) passing said second solution over activated carbon;
   (G) adding a strong mineral acid to said second solution in an amount approximately stoichiometric with said sodium salt of 2,4,5-trifluorobenzoic acid, whereby 2,4,5-trifluorobenzoic acid precipitates; and
   (H) collecting said precipitated 2,4,5-trifluorobenzoic acid.

2. A method according to claim 1 wherein said strong mineral acid is sulfuric acid.

3. A method to claim 1 wherein said second solution is about 10 to about 20 wt % solids.

* * * * *